(12) United States Patent
Isenberg et al.

(10) Patent No.: US 6,752,802 B1
(45) Date of Patent: Jun. 22, 2004

(54) METHOD AND APPARATUS FOR THE PREVENTION OF ENDOMETRIAL HYPERPLASIS AND UTERINE CANCER

(75) Inventors: Richard Isenberg, Gladwyne, PA (US); Joel S. Lippman, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 119 days.

(21) Appl. No.: 10/191,134

(22) Filed: Jul. 9, 2002

Related U.S. Application Data
(60) Provisional application No. 60/303,964, filed on Jul. 9, 2001.

(51) Int. Cl.$^7$ .............................................. A61B 18/04
(52) U.S. Cl. ......................... 606/28; 607/104; 607/105
(58) Field of Search ........................ 606/20–23, 27–29, 606/41, 45, 49; 607/96, 98, 99, 101, 102, 104, 105, 113, 114, 138; 514/178

(56) References Cited

U.S. PATENT DOCUMENTS

| | | | | |
|---|---|---|---|---|
| 5,451,208 A | * | 9/1995 | Goldrath | 604/515 |
| 6,197,351 B1 | * | 3/2001 | Neuwirth | 424/618 |
| 6,265,393 B1 | * | 7/2001 | Heinrichs | 514/178 |

* cited by examiner

*Primary Examiner*—Roy D. Gibson

(57) ABSTRACT

A method for treating endometrial hyperplasia or uterine cancer in menopausal women including performing endometrial ablation in a menopausal woman to thereby ablate substantially all of the endometrium, and administering a hormone therapy of unopposed estrogen. A method is also provided including performing endometrial ablation in a menopausal woman using a thermal ablation technique, and administering a hormone therapy comprising unopposed estrogen.

6 Claims, 2 Drawing Sheets

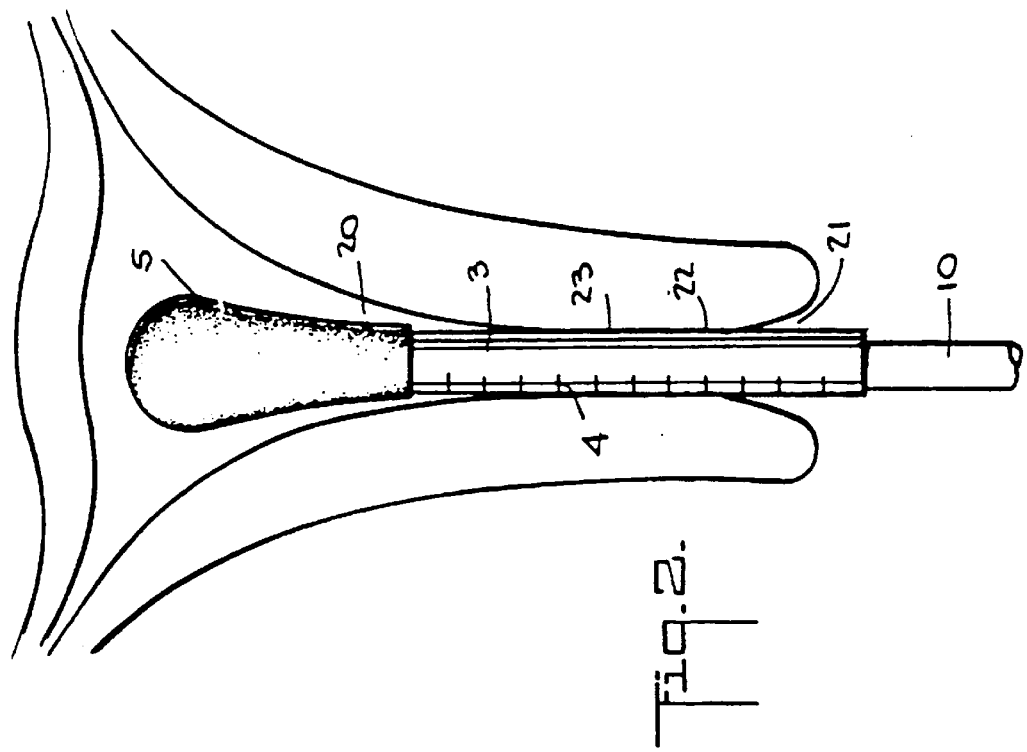
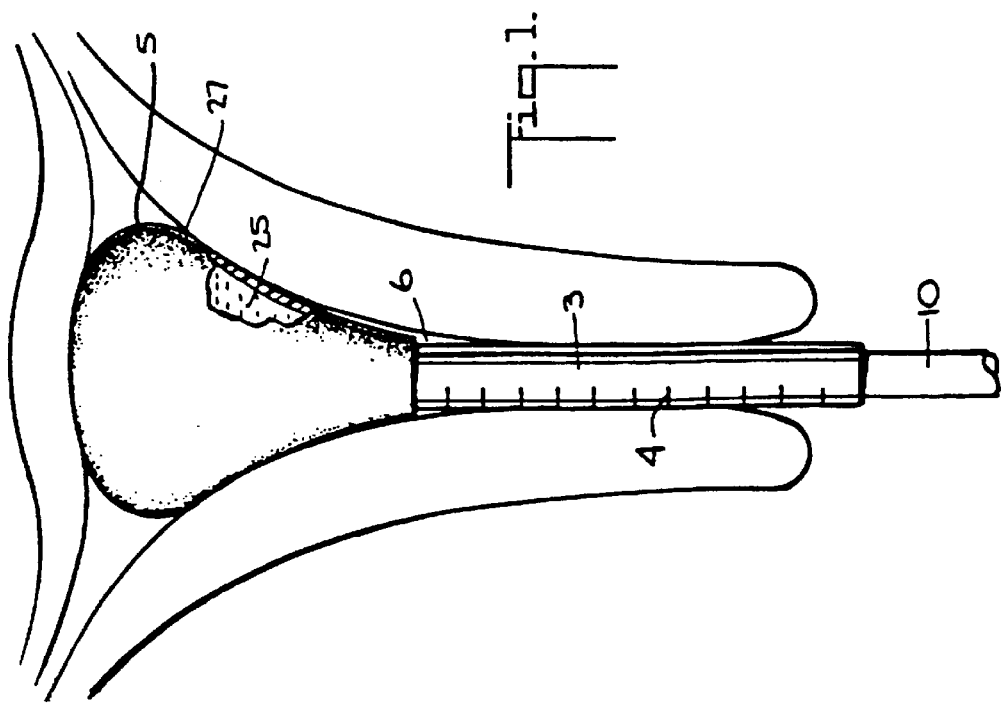

METHOD AND APPARATUS FOR THE PREVENTION OF ENDOMETRIAL HYPERPLASIS AND UTERINE CANCER

CROSS REFERENCE TO RELATED APPLICATIONS

The present invention claims the benefit of earlier filed U.S. provisional patent application, serial No. 60/303,964, filed on Jul. 9, 2001, which is incorporated herein by reference.

FIELD OF THE INVENTION

The present invention relates generally to a method for treating endometrial hyperplasia or uterine cancer in menopausal women, and more particularly to such a method that involves performing endometrial ablation in combination with unopposed estrogen hormone therapy.

BACKGROUND OF THE INVENTION

Female patients are often faced with conditions that may make them susceptible to endometrial hyperplasia or cancer. Included in these conditions are genetics, hormonal and chemotherapies such as Tamoxifen for breast cancer, and hormone replacement therapies such as estrogen or estrogen-progestin therapy. Hormone replacement therapies are often recommended for female patients that are perimenopausal. Perimenopausal patients are defined as premenopausal patients that are in transition to becoming menopausal. These patients exhibit the typical symptoms of the transition to menopause. Perimenopause is the last stage of premenopause. Premenopausal is defined as those patients that have not reached menopause. Menopausal and postmenopausal are synonymous terms. Patients that have reached menopause no longer have menstrual cycles. The benefit of hormone replacement therapy is that it mitigates many of the undesirable symptoms associated with the perimenopausal period. These symptoms include—hot flashes, vaginal dryness, dyspareunia, increased urinary frequency, and mood swings. Hormone replacement therapies are also recommended for menopausal female patients to address disorders of aging. These can include osteoporosis, coronary artery disease and potentially Alzheimer disease and colon cancer.

Estrogen provides the primary benefit in hormone therapy. However, it has been associated with endometrial hyperplasia and sometimes cancer. To minimize these undesirable side-effects, progestin is often administered along with estrogen. While progestin does help to minimize the undesirable effects of estrogen it has its own risks and side effects. Progestin also tends to antagonize and reduce the desired beneficial effects of estrogen. Often, patients will refuse treatment or take themselves off treatment because of the deleterious aspects of progestin. Risks include reduction of estrogen benefit on heart (i.e., reduces estrogen benefit in addressing coronary artery disease) by altering lipid profile. Progestin also causes irregular menstrual bleeding. There is also evidence that progestin increases the risk of breast cancer. Other side effects include bloating, breast tenderness, fluid retention and mood swings. In many regards progestin antagonizes the benefits of estrogen.

To summarize, estrogen treats menopausal symptoms and reduces risk of heart disease, osteoporosis and possibly Alzheimer's Disease and colon cancer, but unopposed estrogen is believed to be associated with increased risk of endometrial hyperplasia and sometimes cancer. Progestin is prescribed to prevent these potential problems. Progestin, however, antagonizes the benefit of estrogen on CVD and causes unpleasant side-effects which constitutes a major reason for discontinuance of hormone replacement therapy.

More recently, there have been drugs developed that may prove to be effective in addressing osteoporosis. However, these drugs do little to address the many other needs of female patients.

Hysterectomy is also a method of preventing endometrial hyperplasia and uterine cancer. This is a highly invasive procedure that also has numerous disadvantages.

Endometrial ablation and resection is a current therapy for perimenopausal female patients for the purpose of minimizing excessive uterine bleeding (Aletebi F A; Vilos G A; Eskandar M A, Journal of the American Association of Gynecologic Laparoscopists November 1999, 6 (4) p435–9; Franchini et al. Gynaecological Endoscopy 1999, 8/2 p111–114). However, it has never been applied to these patients for the purpose of minimizing, reducing or eliminating endometrial hyperplasia and/or uterine cancer.

For the purposes of this disclosure, endometrial ablation is defined as the destruction and removal of endometrial tissue. This may be achieved by the use of laser, thermal, cryotheraputic, ultrasound, radio frequency, electrical, electromagnetic, microwave, roller ball electrodes, loop electrodes, chemical, photochemical, mechanical or any other suitable means.

Postmenopausal women with abnormal uterine bleeding (AUB) and hyperplasia without atypia have been treated with transcervical hysteroscopic endometrial resection (Cianferoni et al., Journal of the American Association of Gynecologic Laparoscopists May 1999, 6 (2) p151–4). This was shown to be an effective treatment in achieving regression of endometrial hyperplasia and preventing its recurrence.

Endometrial ablation and resection therapy has also been applied to female patients in perimenopause and postmenopause that experience excessive uterine bleeding in order to address bleeding disorders that could not be treated by modification of steroid dosages during sequential hormone replacement therapy (Romer, Gynecologic and Obstetric Investigation, 1999, 47 (4), p255–7). In these patients there was no intrauterine cause for the bleeding. Following endometrial ablation, patients received a combined hormone replacement therapy and remained amenorrheic.

One study has been performed in postmenopausal women to determine whether women who have undergone transcervical resection of the endometrium could subsequently receive hormone therapy consisting of unopposed estrogen. Istre et al. (Obstetrics and Gynecology November 1996, 88 (5) p767–70). Istre et al. reported the use of a particular type of endometrial ablation, transcervical resection of the endometrium, of sixty-two postmenopausal women. Both groups were administered continuous hormone replacement therapies. One therapy was 17-beta-estradiol 2 mg alone and the other was 17-beta-estradiol 2 mg combined with norethisterone 1 mg. However, this study concluded that postmenopausal hormone replacement therapy in patients who have undergone transcervical resection of the endometrium should include progestin for protection of the endometrium. Aspects of this study teach away from the approach proposed by this invention.

While perimenopausal and postmenopausal women have been treated with various forms of endometrial ablation (generally for treatment of unwanted bleeding), it has never been a therapy used specifically to prevent endometrial hyperplasia and/or uterine cancer. Further, it has never been discovered that certain endometrial ablation techniques can be used in combination with unopposed estrogen hormone therapy to prevent enodmetrial hyperplasia and/or uterine cancer.

Therefore, there is a need for a better method of treatment for female patients that are susceptible to developing endometrial hyperplasia and/or endometrial cancer. There is also a need for a way to minimize or eliminate the amount of progestin that is required to reduce unwanted side effects of estrogen, and also allow for the retention of the uterus.

SUMMARY OF THE INVENTION

One object of this invention relates to a method and apparatus of treatment for female patients having a uterus. In particular, the invention relates to a treatment that reduces, minimizes or eliminates the onset of endometrial hyperplasia and/or uterine cancer. The treatment is affected by the alteration of at least a part of the endometrial lining of the uterus. Most particularly, the invention relates to ablation of the endometrial lining by techniques that ablate substantially all of the endometrial lining, followed by unopposed estrogen therapy.

In particular, a method is provided for treating endometrial hyperplasia or uterine cancer in menopausal women including performing endometrial ablation in a menopausal woman to thereby ablate substantially all of the endometrium, and administering a hormone therapy comprising unopposed estrogen. According to one embodiment, the performing step is performed using a thermal ablation technique. According to another embodiment, the performing step is performed using a heated fluid in the uterine cavity. According to yet another embodiment, the performing step is performed using a heated fluid within a distendable bladder that substantially conforms to an interior shape of the uterus.

In yet another embodiment, a method is provided for treating endometrial hyperplasia or uterine cancer in menopausal women including performing endometrial ablation using a thermal ablation technique, and administering a hormone therapy comprising unopposed estrogen. In another embodiment, the thermal ablation technique is a heated balloon thermal ablation technique.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 1 depicts a distendable bladder for use in endometrial ablation that has been inserted into and inflated within a uterus of a patient;

FIG. 2 depicts the distendable bladder of FIG. 1 prior to inflation; and

DETAILED DESCRIPTION OF THE INVENTION

Figure 3:
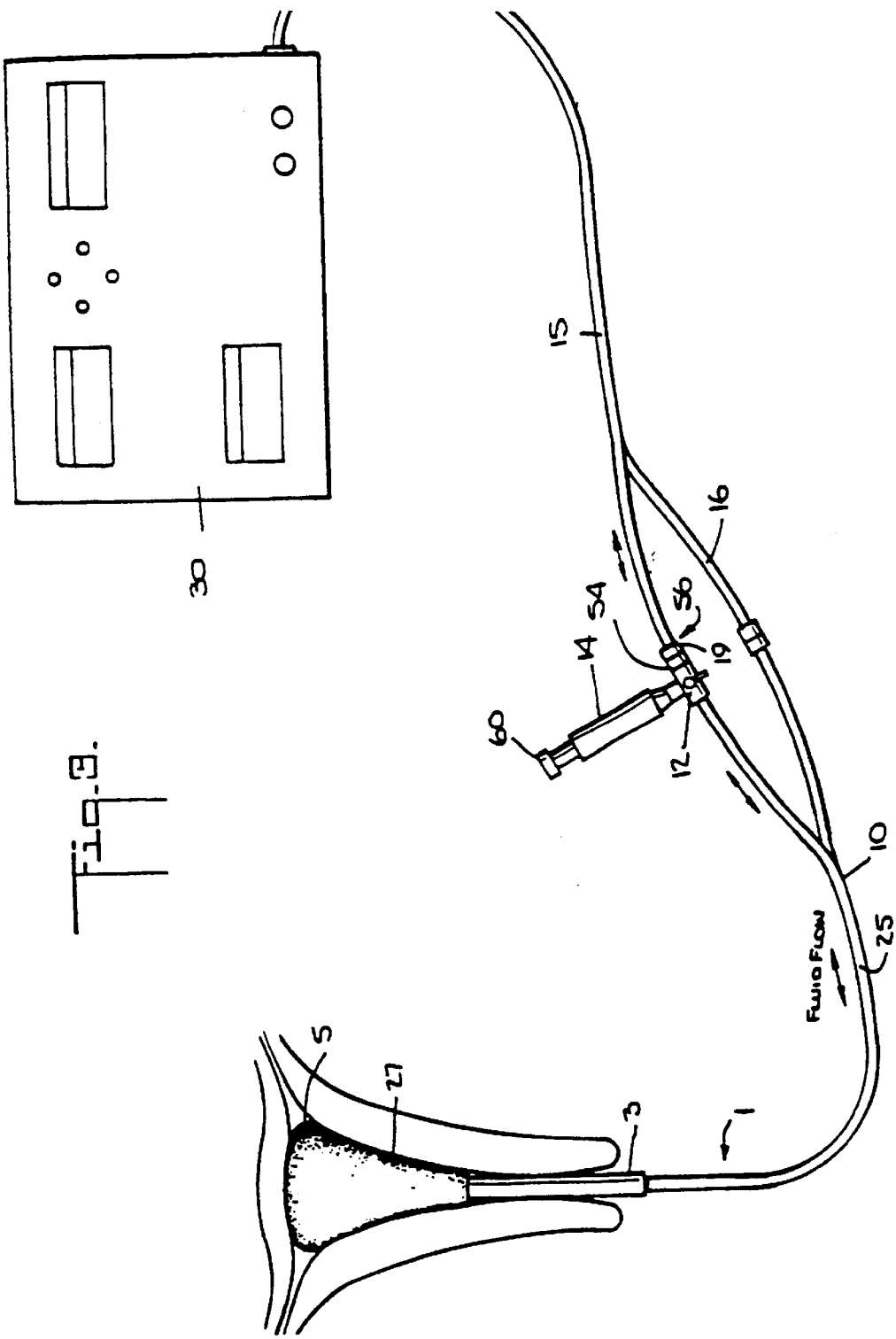
FIG. 3 is a schematic illustration of a thermal ablation system for use with the present invention.

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention and are not intended to limit the scope of the invention in any manner.

Patients suitable to receive treatment according to the present invention are peri-menopausal and post-menopausal female patients (collectively referred to hereinafter as post-menopausal) that are (a) candidates for estrogen or estrogen-progestin hormone replacement therapy (HRT) and/or (b) that are already undergoing HRT are selected. Patients may be either symptomatic with symptoms of perimenopause/menopause (such as hot flashes, vaginal dryness, dyspareunia, increased urinary frequency, and mood swings), or asymptomatic. Patients may be desirous of using HRT to reduce the risk of disorders of aging (such as osteoporosis, coronary artery disease and potentially Alzheimer disease and colon cancer) or not desirous of such benefit. Patients may be on an established regimen and dosage of HRT, undergoing modification of HRT regimen and dosage to address adverse effects of HRT or other reasons, planning initiation of HRT or just considering the option of HRT. Patients may be on unopposed estrogen or any combination of estrogen and progestin, with or without androgen. Patients on HRT may be on cyclic or continuous dosing regimens. Patients on HRT may be experiencing erratic (break through) bleeding, intermenstrual bleeding, heavy menses (menorrhagia), light menses, normal menses, or no bleeding.

These patients would undergo endometrial ablation utilizing hysteroscopic or global endometrial ablation techniques that are effective in ablating substantially all of the endometrium. Endometrial resection techniques that are currently known are not suitable, as these techniques do not remove a sufficient amount of the endometrium, but rather leave behind intact "strips" or portions of the endometrium. It is believed that this remaining endometrium tends to form the basis for regrowth, and thus subsequent increased risk for endometrial hyperplasia and uterine cancer. Accordingly, endometrial ablation techniques according to the present invention should be more efficient in removing the endometrium to be effective. Preferably, substantially all of the endometrium should be removed, but it is believed that removal of 90 percent or more of the endometrium is effective.

According to a preferred embodiment, thermal ablation techniques are employed, and in particular, thermal ablation using the THERMACHOICE Uterine Balloon Therapy System (trademark of Ethicon, Inc.), manufactured and sold by Ethicon, Inc. of Somerville, N.J. THERMACHOICE is a heated balloon therapy. This system is a software-controlled device designed to ablate uterine tissue by thermal energy. The system is includes a single-use balloon catheter, a reusable controller, and umbilical cable, as shown schematically in FIG. 3. The process of using this type of device starts by working with an assembled device (e.g., umbilical cable attached to both the balloon and controller, pressure line connected to the controller, impeller cable connected to the controller). The uterus is examined using ultrasound. If necessary, the cervix is dilated. The balloon is moistened and inserted to the fundus in a substantially deflated condition (see FIG. 2). A trumpet valve is depressed to slowly inject plain 5% dextrose in water solution into the balloon to inflate the balloon and to achieve a pressure between 160–180 mm Hg (the higher the better) (see FIG. 1). The amount of plain 5% dextrose in water solution is adjusted to maintain the desired pressure. Once pressure is stabilized, the therapeutic treatment is initiated. This includes heating, and maintaining, the plain 5% dextrose in water solution to approximately 87 degrees C (187 degrees F.) for a period of 8 minutes. Following the completion of the treatment, the balloon is deflated and the catheter is removed. Additional details relating to heated balloon therapy can be found in U.S. Pat. Nos. 4,949,718, 5,108,808, 5,704,934, and 5,800,493; and U.S. patent application Nos. 09/749,077 and 09/749,180, both filed on Dec. 27, 2000, which are incorporated herein by reference.

Other ablation techniques may also be used so long as they remove a sufficient amount of the endometrium as described above.

Use of a balloon thermal ablation technique to perform endometrial ablation is also advantageous as it is less likely to mask endometrial hyperplasia or cancer should it occur. An important aspect of treatment in the post-menopausal population is ensuring that if endometrial hyperplasia does occur, that it will present in a manner that will allow diagnosis of the condition. Endometrial hyperplasia and cancer are most commonly found through presentation of blood in a postmenopausal patient. Balloon thermal ablation, such as with the THERMACHOICE product, followed by unopposed estrogen will allow the small percentage of women who may develop hyperplasia to present in the usual manner by having a high incidence of leaving an unobstructed pathway through the uterine cavity and cervix for the blood to exit. Diagnosis of hyperplasia or cancer can then be confirmed through biopsy through the same unobstructed pathway. Other technologies, such as rollerball, have a low incidence of leaving an unobstructed pathway and therefore present a greater safety risk for the patients developing hyperplasia. They also present greater challenges to confirm the diagnosis due to obstructed access to the cells.

THERMACHOICE achieves low rates of cervical stenosis by having a low energy delivery to the cervix from the catheter inherent to the design of using a fixed volume of fluid in the uterine cavity. The uterine body pathway is kept clear due to the healing pattern resulting from using an atraumatic balloon surface delivering direct thermal energy combined with high pressure distension holding cavity open during treatment.

Following endometrial ablation, patients are treated with HRT. Patients may be treated with unopposed estrogen or any combination of estrogen/progestin. Patients may receive hormone therapy in a continuous, cyclic or intermittent fashion, at high or low doses, for long or short duration, early or late in their post operative period or any time thereafter. Estrogen may be delivered orally, transdermal, parenterally, vaginally or by any other suitable means. Progestin may be synthetic or natural delivered on an infrequent cyclic basis (preferred) or continuous basis with a cyclic dosing as frequently as monthly or infrequently as once per year. For example, a patient receiving estrogen therapy may also receive ten days of a low dose of progestin delivered every three to four months. According to one embodiment, the patient may receive PREMARIN® brand conjugated estrogen tablets for oral administration, which is a product of Wyeth® BioPharma of Philadelphia, Pa. Dosages may vary from 0.3 to 1.25 mg/day, depending on the patient.

Patients may be evaluated for the presence of persistent endometrium by non-invasive techniques such as ultrasound, saline infused sonography, magnetic resonance imaging, hysterosalpingraphy or other radiographic studies, invasive techniques such as hysteroscopy, or provocative testing such as progestin withdrawl tests.

While radio frequency electrode and global thermal ablation approaches are described, this invention is not limited to these approaches. Other approaches may include, but are not limited to, treatment with other means of hysteroscopic endometrial resection and/or ablation, laser vaporization, electrosurgical vaporization, desiccation and fulgeration, cryotherapy, microwave ablation, chemical removal or treatment, photosensitization and immunologic treatments. Any treatment that effects the removal and or alteration of the endometrial lining is considered within the scope of this invention.

A side benefit to this approach is that it can halt uterine bleeding in patients on hormone replacement therapy and other therapies such as Tamoxifen. This approach may also be effective in treating simple and complex hyperplasia without atypia. This approach may be effective in reducing the risk of endometrial hyperplasia and endometrial cancer in perimenopausal and postmenopausal women not taking HRT.

It will be apparent from the foregoing that, while particular forms of the invention have been illustrated and described, various modifications can be made without departing from the spirit and scope of the invention. Accordingly, it is not intended that the invention be limited, except as by the appended

What is claimed is:

1. A method for treating endometrial hyperplasia or uterine cancer in menopausal women comprising:

performing endometrial ablation in a menopausal woman to thereby ablate substantially all of the endometrium; and administering a hormone therapy comprising unopposed estrogen.

2. The method according to claim 1, wherein the performing step is performed using a thermal ablation technique.

3. The method according to claim 2, wherein the performing step is performed using a heated fluid in the uterine cavity.

4. The method according to claim 3, wherein the performing step is performed using a heated fluid within a distendable bladder that substantially conforms to an interior shape of the uterus.

5. A method for treating endometrial hyperplasia or uterine cancer in menopausal women comprising:

performing endometrial ablation in a menopausal woman using a thermal ablation technique; and administering a hormone therapy comprising unopposed estrogen.

6. The method according to claim 5, wherein the thermal ablation technique is a heated balloon thermal ablation technique.

* * * * *